Figure 1:
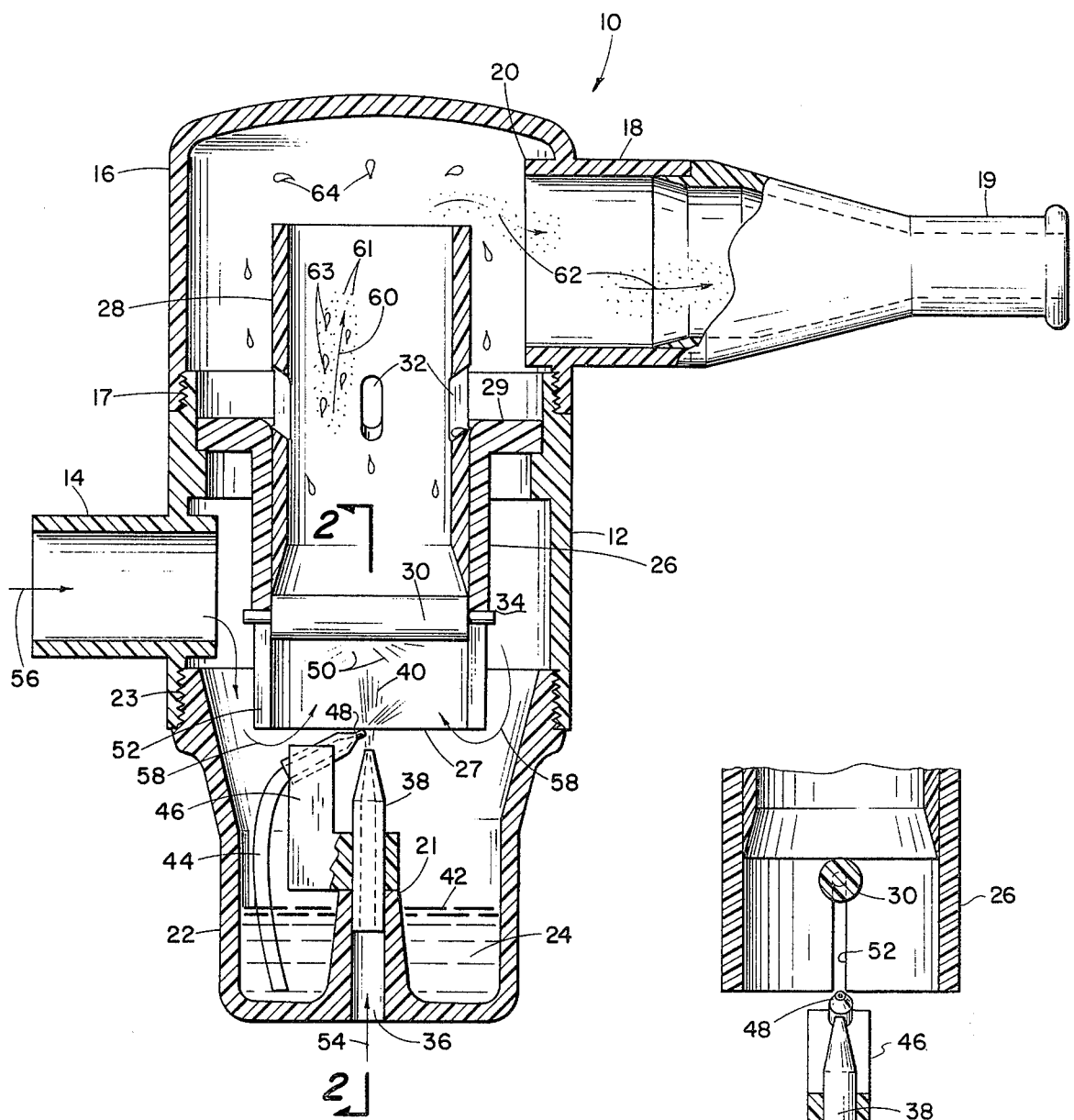

United States Patent [19]

Glenn

[11] 4,007,238
[45] Feb. 8, 1977

[54] NEBULIZER FOR USE WITH IPPB EQUIPMENT

[76] Inventor: Joseph G. Glenn, Rte. 1 Box 1221, Broken Arrow, Okla. 74012

[22] Filed: Feb. 25, 1976

[21] Appl. No.: 661,366

[52] U.S. Cl. .............................. 261/78 A; 128/194; 239/338; 261/DIG. 65
[51] Int. Cl.² ................. A61M 15/00; A61M 11/06
[58] Field of Search .................. 261/78 A, DIG. 65; 128/193, 194; 239/124, 314, 318, 335, 338, 340, 343, 422

[56] References Cited

UNITED STATES PATENTS

| | | | |
|---|---|---|---|
| 2,421,359 | 5/1947 | Sutherland | 261/78 A |
| 2,605,764 | 8/1952 | Adams et al. | 128/194 |
| 2,869,188 | 1/1959 | Cameto | 239/338 |
| 3,018,971 | 1/1962 | Cheney | 239/335 |
| 3,097,645 | 7/1963 | Lester | 239/335 |
| 3,172,406 | 3/1965 | Bird et al. | 128/194 |
| 3,864,326 | 2/1975 | Babington | 261/78 A |

FOREIGN PATENTS OR APPLICATIONS

| | | | |
|---|---|---|---|
| 704,070 | 2/1954 | United Kingdom | 239/338 |
| 958,867 | 5/1964 | United Kingdom | 239/338 |

*Primary Examiner*—Tim R. Miles
*Assistant Examiner*—Gregory N. Clements
*Attorney, Agent, or Firm*—Head, Johnson & Chafin

[57] ABSTRACT

A nebulizer for use with IPPB equipment comprising a cylindrical housing closed at top and bottom, with an air inlet through the side wall of the housing, and an outlet through the side wall near the top of the housing. The outlet carries a mouthpiece. The bottom portion of the housing comprises a reservoir for liquid medication. There is an axial cylindrical chimney positioned inside the housing, with a skirt which hangs below the position of the inlet so that incoming air from the IPPB flows downward around the chimney, up inside of the chimney, out of the top of the chimney, and sideways into the outlet pipe. Positive pressure air is provided to a vertical nozzle positioned in the bottom of the housing creating a high velocity stream of air which flows over the end of a capillary tube, which dips into the medication in the base portion. The high velocity air jet causes the liquid medication to be inducted through the capillary and to be picked up by the flowing air as droplets of liquid to impinge on a horizontal cylindrical target positioned immediately above the nozzle, so that the liquid droplets are broken into many fine droplets, which are then picked up by the air flow, and carried upward through the chimney and to the outlet pipes.

4 Claims, 2 Drawing Figures

NEBULIZER FOR USE WITH IPPB EQUIPMENT

BACKGROUND OF THE INVENTION

This invention lies in the field of breathing devices. More particularly, it concerns the design and construction of a nebulizer, or atomizer, for liquid medication, which is to be administered through the air supply to a patient.

In the prior art, there have been a large number of patents issued for various types of nebulizers, all of which have one problem or another. The principal difficulty of most atomizers, or nebulizers, is the matter of size of liquid particles that are produced. It is generally conceded that any droplets of size larger than 10 microns, and particularly the large drops of 1/16 inch or larger, are trapped on the walls of the mouth or throat and never pass into the lungs. For the medication to reach the smaller passages in the bronchial tubes and lungs, the size of liquid particles must be in the range of 0.5 to 5 microns.

Various means have been provided in the past for the purpose of creating fine mists of liquid but have not been able to continuously provide such a fine mist as is desired.

It is therefore a primary object of this invention to provide a nebulizer which, with a supply of pressurized air will product a fine mist of liquid droplets, which can be picked up by the air supply provided by an IPPB apparatus, to provide medication to the lungs of a patient.

It is a further object of this invention to provide a nebulizer which will produce a fine droplet mist and which has means for separating out the larger sizes of particles, in case they are produced, so that they will settle out, be trapped, and returned to the reservoir of liquid, instead of passing on to the patient.

SUMMARY OF THE INVENTION

These and other objects are realized and the limitations of the prior art are overcome in this invention by providing a vertical cylindrical housing which is closed at the top by means of a cap, which includes side tube leading to a mouthpiece, and is closed at the bottom by means of a cup which is used as a reservoir of liquid medication. The air supply, as from an IPPB apparatus, is introduced through the sidewall of the central section of the housing. A cylindrical tube or chimney is positioned coaxially inside the housing, with a skirt which hangs below the position of the inlet air tube, which causes the flow of breathing air to come in through the inlet air tube down around the outside of the skirt, and up into the chimney, and out of the top end, sideways, into the outlet pipe and mouthpiece.

Positive pressure air is provided through an axial tube and nozzle in the base, so that a high velocity stream of air blows axially, vertically over the end of a capillary tube, which dips into the liquid medication. Liquid is drawn up the capillary and is carried by air stream in the form of droplets, against a horizontal cylindrical target. Here the drops are broken up into fine droplets and the vertically rising air flowing past the target, carries the liquid mist up the chimney and out through the mouthpiece. Means are provided for the settling of large droplets around the outside of the chimney and the liquid then passes through a plurality of openings in the wall of the chimney so that the liquid falls back into the reservoir in the bottom of the cup.

BRIEF DESCRIPTION OF THE DRAWINGS

These and other objects and advantages of this invention and a better understanding of the principles and details of the invention will be evident from the following description taken in conjunction with the appended drawing, in which:

FIG. 1 is a vertical cross-section which illustrates the construction of the nebulizer of this invention.

FIG. 2 is a cross-section showing a different view of the nozzle and target portion of the apparatus taken across plane 2—2 of FIG. 1.

DESCRIPTION OF THE PREFERRED EMBODIMENT

Referring now to the drawing, there is shown in vertical cross-section, one embodiment of this invention. It is indicated generally by the numeral 10, and includes a cylindrical housing 12 which is normally positioned with its axis vertical. There is a side tube 14 through the wall of the housing 12 for the purpose of drawing breathing air from the IPPB apparatus, not shown, in accordance with arrow 56. A cap portion 16, which extends the cylindrical housing vertically, and closes off the top, is attached as by threads 17, to the top end of the housing 12. The top cap 16 has an outlet pipe 18 which projects through the wall of the cap, and extends inward of the inner surface of the cap 20. A mouthpiece 19 is attached to the side tube 18, for use by the patient.

The bottom end of the housing 12 is closed by means of a cup 22 which is attached, as by threads 23, to the bottom of the housing 12. A central post 21 of the cup 22 carries a passage 36 into which is inserted a nozzle 38. Air under pressure is provided in accordance with arrow 54 to the central opening 36. A capillary tube 14 has its bottom end immersed below the surface 42 of the liquid 24, and terminates at its top in an endpiece 48, which is held in position by arm 46 attached to the post 21. The stream 40 of pressurized air 54 flowing through the nozzle at high velocity, will cause the induction of liquid from the reservoir 24, through the tube 44, to the open end 48 where it will be picked up by the high velocity air stream 40 and caused to impinge at high velocity on the horizontal cylindrical target 30. The result is a breaking up of the droplets into many very fine droplets or mist 50, which is then carried by the vertically rising air in accordance with arrows 58, up through the chimney 26 in accordance with arrow 60, for example.

The arrow 60 is shown as carrying very fine droplets 61 and some larger droplets 63. As the air flow turns horizontally, in accordance with arrows 62, the larger droplets are caused to leave the flowing stream as 64, and they then settle down, and flow down inside of the cylindrical wall 28, to the reservoir liquid 24. If they fall down outside of the cylinder 28, they then pass through the opening 32 into the center of the chimney and back into the reservoir 24.

The air flow from the IPPB appartus shown by arrow 56 flows in the annular space 34 around the tubular skirt 26, down under the bottom edge 27, and up inside of the skirt 26. There is a tubular extension 28 which rises as a chimney up inside of the skirt 26. The smaller diameter of the opening inside of the chimney 28 causes a relatively high velocity of air flow in accordance with arrows 58 and 60, which tend to carry the droplets away from the target area 30. As the air flow turns to the horizontal at the top of the chimney 28, the larger drops are thrown out and the air with a fine mist of small droplets flows horizontally through the outlet tube 18, to the mouthpiece 19 and to the patient. The internal extension 20 of the outlet pipe 18 provides assurance that liquid medication which might drip down the wall of the cap 16 does not find its way into the outlet pipe 18 but continues down to the shelf 29 and through the openings 32 to the inside of the chimney 28, and down to the reservoir 24.

The volume of air provided in accordance with arrow 54, through the nozzle 38, is a small part of the total flow 56 of air from the IPPB to the patient. While the air flow 56 continues, the mist of fine droplets formed at the target 30 are carried up through the chimney and through the mouthpiece, etc. When the flow 56 stops, for exhalation by the patient, the air flow 54 continues, maintaining in the region of the target 30 a very fine mist of micron sized droplets, so that when air flow 56 again starts by the IPPB apparatus, it can pick up the mist and carry it to the patient.

Figure 2:
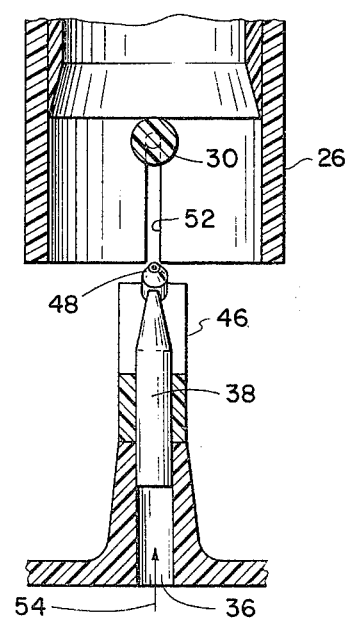

While the outlet pipe 44 is shown in FIGS. 1 and 2 as horizontal, it will be clear that the pipe could alternatively be vertical, if desired, as shown by dashed line 44' in FIG. 1, thereby permitting entrained water drops to drain back into the vessel 12. It would preferably still be placed near the wall opposite edge 40 of baffle 38.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed:

1. A nebulizer for use with IPPB appartus comprising:
    a. a cylindrical housing with axis vertical, an air inlet tube extending horizontally through the wall of said housing;
    b. top closure means closing the top end of said housing, an outlet tube passing through the wall of said top closure means;
    c. a bottom cup removably attached to said housing for closing the bottom end of said housing, and storing a supply of liquid medication; a post in the base of said cup, an opening through said post, and an orifice closing the top end of said opening;
    d. means to supply air under pressure to said nozzle to create a vertical jet of air;
    e. capillary tube means attached to said post, the bottom end immersed in liquid medication in said cup, the top end fixed in position in said air jet, whereby the flow of air will cause liquid to be drawn up inside said capillary and to form droplets at the top end, which are picked up by said air jet;
    f. horizontal cylindrical target means mounted above said air jet, whereby said jet and liquid droplets will impinge on said target and said droplets will be broken into micron size droplets;
    g. an axial cylindrical chimney inside said housing having a skirt extending below said inlet tube, the top end of said chimney extending almost to the top closure, the annulus between said chimney and said housing closed by a mounting flange, a plurality of openings through the wall of said chimney above said flange.

2. The nebulizer as in claim 1 in which said target is supported in said skirt.

3. The nebulizer as in claim 1 in which said outlet tube extends inside of the wall of said top closure.

4. The nebulizer as in claim 1 in which said nozzle and said post are axially positioned in said cup.

* * * * *